US012766237B2

(12) United States Patent
Gliner et al.

(10) Patent No.: US 12,766,237 B2
(45) Date of Patent: Oct. 20, 2026

(54) PHACOEMULSIFICATION VACUUM SURGE DETECTION WITH CORRELATED VACUUM AND PRESSURE READINGS

(71) Applicant: JOHNSON & JOHNSON SURGICAL VISION, INC., Irvine, CA (US)

(72) Inventors: Vadim Gliner, Haifa (IL); Eran Haas, Haifa (IL); Assaf Govari, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 728 days.

(21) Appl. No.: 18/197,412

(22) Filed: May 15, 2023

(65) Prior Publication Data

US 2024/0382664 A1 Nov. 21, 2024

(51) Int. Cl.
*A61M 1/00* (2006.01)
*A61F 9/007* (2006.01)

(52) U.S. Cl.
CPC ......... *A61M 1/777* (2021.05); *A61F 9/00745* (2013.01); *A61M 1/73* (2021.05); *A61M 1/74* (2021.05); *A61B 2217/005* (2013.01); *A61B 2217/007* (2013.01); *A61M 2205/3341* (2013.01); *A61M 2205/50* (2013.01)

(58) Field of Classification Search
CPC .......... A61M 1/777; A61M 1/73; A61M 1/74; A61M 2205/3341; A61M 2205/50; A61M 1/77; A61F 9/00745; A61B 2217/005; A61B 2217/007
See application file for complete search history.

(56) References Cited

U.S. PATENT DOCUMENTS 8,668,665 B2 3/2014 Gerg et al.
2005/0209560 A1* 9/2005 Boukhny ............ A61M 3/0258 604/122
2005/0209561 A1* 9/2005 Gordon .................. A61M 1/77 604/119
2010/0130914 A1 5/2010 Gordon et al.
2010/0268388 A1 10/2010 Boukhny et al.
2020/0297534 A1* 9/2020 Boukhny ............ A61F 9/00745

FOREIGN PATENT DOCUMENTS

AU 2013202059 A1 4/2013
WO 2022136986 A1 6/2022

OTHER PUBLICATIONS

U.S. Appl. No. 17/130,409, filed Dec. 22, 2020, and titled, “A module for Aspiration and Irrigation Control”.

* cited by examiner

*Primary Examiner* — James D Ponton

(57) ABSTRACT

A method includes calculating in real-time a correlation between vacuum readings and pressure readings of respective aspiration and irrigation channels of a phacoemulsification handpiece engaged in a phacoemulsification procedure in an eye. Upon detecting an increase in the vacuum readings and an increase in the pressure readings, a current level of the correlation is checked. Provided that the current level of the correlation is above a given value, an anti-vacuum surge (AVS) mechanism is activated, the AVS mechanism fluidly coupled with at least one of the irrigation and aspiration channels.

8 Claims, 2 Drawing Sheets

PHACOEMULSIFICATION VACUUM SURGE DETECTION WITH CORRELATED VACUUM AND PRESSURE READINGS

FIELD OF THE DISCLOSURE

The present disclosure relates generally to phacoemulsification apparatuses and probes, and particularly to apparatuses and methods for control of intraocular pressure (IOP).

BACKGROUND OF THE DISCLOSURE

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

The present disclosure will be more fully understood from the following detailed description of the examples thereof, taken together with the drawings in which:

DETAILED DESCRIPTION OF EXAMPLES

Overview

Figure 1:
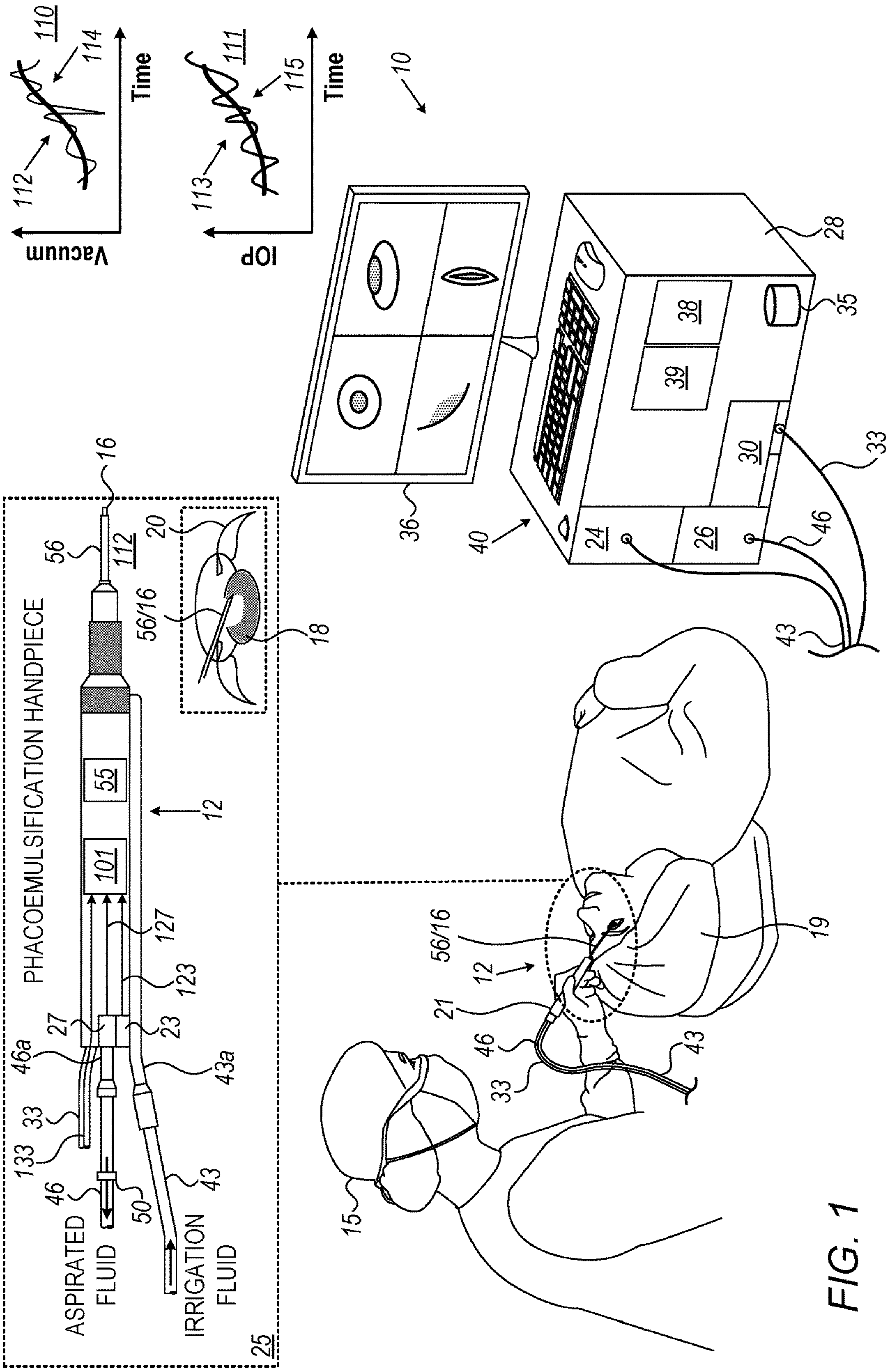
FIG. 1 is a schematic, pictorial view, along with an orthographic side view, of a phacoemulsification apparatus, in accordance with an example of the present disclosure.

During phacoemulsification of an eye lens, if an emulsified lens particle fully blocks the inlet of the aspiration tip, a high vacuum occurs in the aspiration line. After the vacuum buildup, when the line becomes unblocked (e.g., by the particle being subsequently sucked into the line), the high vacuum in the line leads to the eye experiencing a surge in aspiration suction power (also called hereinafter a "vacuum surge") with potentially traumatic consequences to the eye as the intraocular pressure (IOP) abruptly falls. For example, exposing the eye to suction power leading to a very low IOP (e.g., below-20 mmHg) may cause the eye chamber to collapse.

A recent solution to the problem of automatically detecting and mitigating vacuum surges is described in U.S. patent application Ser. No. 17/130,409, filed on Dec. 22, 2020, and titled, "A module for Aspiration and Irrigation Control," whose disclosure is incorporated herein by reference. The application discloses an anti-vacuum surge (AVS) mechanism (e.g., an AVS module) coupled with the phacoemulsification probe that prevents a sudden vacuum increase being transferred to the eye in case of occlusion break (i.e., prevents vacuum surge). For example, the module can mitigate the vacuum surge by closing off a connection from the aspiration line to the eye at the distal side of the module as soon as vacuum surge is detected.

Timely detection of the onset of a vacuum surge, however, is difficult due to inherently noisy pressure and/or vacuum level sensor readings. Noisy readings, or fluctuations, can be caused by various reasons, such as variations in the irrigation flow or in the amount of emulsified lens particles that are aspirated through the aspiration tip. In addition, the small volume of the lens capsule makes such variations inevitable. When using a tip (e.g., a hollow needle) with a small diameter, noise is amplified (due to sharp drops in pressure flow through the tip) causing large peaks to occur in the readings. Additional sources of noise are kinks in the aspiration tube and vibrations due to pump motion.

The fluctuations in pressure readings can resemble an onset of a vacuum surge and generate an unacceptable rate of false positive activations of the AVS module. Frequent aspiration blockages by AVS module activations may cause the physician to perform the phacoemulsification process too slowly, thereby leading to practical ineffectiveness.

The inventors observed that, although detecting a vacuum surge based on irrigation pressure readings is accurate, it also produces false-positive detections. Detecting a vacuum surge based on aspiration vacuum reading is less accurate, but on the other hand produces fewer false-positive detections.

Examples of the present disclosure that are described hereinafter utilize the aforementioned observations by the inventors. The examples provide methods and apparatuses that use aspiration vacuum readings, irrigation pressure readings, and the correlation between them, to identify a vacuum surge. If a processor detects an increase in aspiration vacuum level and a sufficiently correlated increase in irrigation pressure (or, equivalently, a sufficiently correlated rise in IOP), the processor activates the AVS module.

The processor estimates the IOP based on irrigation pressure and irrigation flow. To this end, a trend in the IOP is monitored during the phacoemulsification procedure and used to predict the IOP forward going (e.g., 100 milliseconds from the current time). The IOP at a future time is predicted (e.g., computed) based on the current IOP as provided by a pressure sensor close to the eye (e.g., in an irrigation channel of the phacoemulsification probe), or in the eye (e.g., on another probe inserted into the eye), and one or more indicators as how the IOP is changing or will change over time. The predicted IOP for the future time is then used to determine a desired flow rate for the irrigation pump to maintain the actual IOP at, or around, a given IOP.

In some examples, the processor activates the AVS module indirectly, by instructing a microcontroller that controls the AVS module. In one example, the microcontroller is integrated in the phacoemulsification handpiece. In other examples, the microcontroller may be integrated into the AVS module, or it can be in a console.

In one example, a processor inside the AVS module calculates a real-time correlation coefficient (CC (e.g., the Pearson correlation coefficient (PCC)) between the vacuum readings and the estimated IOP. In another example the processor is external (e.g., located in the console).

The processor monitors changes in the vacuum level in the aspiration line (or in a channel inside the phacoemulsification handpiece). The monitoring consists of fast- and slow-moving averages of the vacuum level. The processor compares the fast-moving average to the slow-moving average and based on the comparison identifies sharp changes in IOP. The processor uses fast-moving average as a current base line pressure (the larger window) and uses the slow-moving average as current pressure (small window). Once a rise in vacuum level is detected, the processor checks the current level of correlation (e.g., one calculated over up to 100 mSec of signal duration) with any observed drop in estimated IOP (e.g., if the CC is lower than a given threshold, where the threshold is the IOP target). Only if the correlation is deemed high enough does the microcontroller activate the AVS mechanism.

The disclosed technique may use a high-resolution (e.g., 32-bit) microcontroller with fast (sub-microsecond) real-time capabilities, digital signal processing, low-power/low-voltage operation, and connectivity, while maintaining a small form factor that enables the integration of such a microcontroller in the phacoemulsification handpiece, for example, the STM32 microcontroller, made by STM, which includes DMA memory.

Using such a microcontroller, the phacoemulsification apparatus avoids delays associated with the need to access the CPU and operate related software/firmware. Instead, the power line is connected to one of the outputs of the STM32 which may be programmed to toggle power between 0/1 (i.e., off/on) based on the vacuum surge identification.

Apparatus Description

FIG. 1 is a schematic, pictorial view, along with an orthographic side view, of a phacoemulsification apparatus 10, in accordance with an example of the present disclosure.

As seen in the pictorial view of phacoemulsification apparatus 10, and in the orthographic side view inset 25, a phacoemulsification probe 12 (e.g., a handpiece) comprises a distal end 112 comprising a needle 16 and a coaxial irrigation sleeve 56 that at least partially surrounds needle 16 and creates a fluid pathway between the external wall of the needle and the internal wall of the irrigation sleeve, where needle 16 is hollow to provide an aspiration channel. Moreover, the irrigation sleeve may have one or more side ports at or near the distal end to allow irrigation fluid to flow toward the distal end of the handpiece through the fluid pathway and out of the port(s).

Needle 16 is configured for insertion into a lens capsule 18 of an eye 20 of a patient 19 by a physician 15 to remove a cataract. While the needle 16 (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Irvine, CA, USA.

In the shown example, during the phacoemulsification procedure a processor-controlled irrigation pump 24 comprised in a console 28 pumps irrigation fluid from an irrigation reservoir (not shown) to the irrigation sleeve 56 to irrigate the eye. The fluid is pumped via an irrigation tubing line 43 running from console 28 to an irrigation channel 43*a* of probe 12. In another example, pump 24 may be coupled with, or replaced by, a gravity-fed irrigation source such as a balanced salt solution bottle/bag. Alternatively, irrigation plump 24 may be located outside of the console 28, e.g., in the handpiece.

Eye fluid and waste matter (e.g., emulsified parts of the cataract) are aspirated via hollow needle 16 to a collection receptacle (not shown) by a processor-controlled aspiration pump 26, also comprised in console 28, using aspiration tubing line 46 running from aspiration channel 46*a* of probe 12 to console 28. In an example, processor 38 controls an aspiration rate of aspiration pump 26 to maintain intraocular pressure (e.g., in case of sub-pressure indicated, for example, by sensor 27) within prespecified limits.

Channels 43*a* and 46*a* are coupled with irrigation line 43 and aspiration line 46, respectively. Pumps 24 and 26 may be any pump known in the art (e.g., a peristaltic pump, a progressive cavity pump, etc.). An interface 39, such as interface comprising electronic circuitry, is configured to receive vacuum readings and pressure readings from sensors (e.g., as indicated by sensors 23 and/or 27), of respective aspiration and irrigation channels of phacoemulsification handpiece 12 engaged in a phacoemulsification procedure in the eye. Using the vacuum readings and the pressure readings, processor 38 controls a pump rate of irrigation pump 24 and aspiration pump 26 to maintain intraocular pressure (IOP) within prespecified limits. Alternatively, aspiration plump 26 may be located outside the console, e.g., in the handpiece.

In the shown example, probe 12 includes an irrigation sensor 23 coupled with irrigation channel 43*a* and an aspiration sensor 27 coupled with an aspiration channel 46*a*. Sensors 23 and 27 may be any sensor known in the art, including, but not limited to, a vacuum sensor or flow sensor, and may be located anywhere along the irrigation/aspiration lines (43/46) or irrigation/aspiration channel (43*a*/46*a*). In an example, sensor measurements (e.g., pressure, vacuum, and/or flow) may be taken close to the proximal end of the handpiece where the irrigation outlet and the aspiration inlet are located, so as to provide processor 38 with an accurate indication of the actual measurements occurring within an eye and provide a short response time to a control loop comprised in a microcontroller 101 comprised in probe 12, as described below.

A vacuum sensor, as discussed herein, includes types of pressure sensors that are configured to provide sufficiently accurate measurements of low sub-atmospheric pressures within a typical sub-pressure range at which aspiration is applied (e.g., between 1 mmHg and 650 mmHg). In an example, the same pressure sensor model is used to measure irrigation pressure and aspiration sub-pressure, using different sensor settings/calibrations.

As further shown, phacoemulsification probe 12 includes one or more piezoelectric crystals (or ultrasound transducer) 55, coupled with a horn (not shown), that drives needle 16 to vibrate in a resonant vibration mode that is used to break a cataract into small pieces during a phacoemulsification procedure. Console 28 comprises a piezoelectric drive module 30 that is controlled by a processor 38, which conveys processor-controlled driving signals via cable 33 to, for example, maintain needle 16 at maximal vibration amplitude. The drive module may be realized in hardware or software, for example, in a proportional-integral-derivative (PID) control architecture.

In some cases, typically to protect against a vacuum surge hazard, the apparatus activates AVS module 50 (seen in inset 25) to disconnect aspiration channel 46*a* from line 46 and aspiration pump 26. AVS module 50 can be autonomous, with a processor inside AVS 50 that receives and processes sensor readings and commands activation of module 50, or module 50 can be commanded from processor 38.

Microcontroller 101 has an interface with wiring 133 running in cable 33 to receive and/or output electrical signals. Using pressure readings received via wiring 123 from sensor 23 and vacuum level reading received via wiring 127 from sensor 27, microcontroller 101 can control AVS module 50, as further described in FIGS. 2 and 3 below.

Processor 38 may receive user-based commands via a user interface 40, which may include setting a vibration mode and/or frequency of the piezoelectric crystal, and setting or adjusting an irrigation and/or aspiration rate of the irrigation pump 24 and aspiration pump 26. Processor 38 may receive user-based commands via a user interface 40, which may include needle 16 stroke amplitude settings and activating irrigation and/or aspiration. In an example, the physician uses a foot pedal (not shown) as a means of control, where pedal position one activates irrigation only, pedal position two activates both irrigation and aspiration, and pedal position three adds needle 16 vibration. Additionally, or alternatively, processor 38 may receive user-based commands from controls located in a handle 21 of probe 12.

In an example, user interface 40 and display 36 may be integrated into a touch screen graphical user interface.

Some or all of the functions of processor 38 may be combined in a single physical component or, alternatively, implemented using multiple physical components. These physical components may comprise hard-wired or programmable devices, or a combination of the two. In some examples, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The apparatus shown in FIG. 1 may include further elements, which are omitted for clarity of presentation. For example, physician 15 typically performs the procedure using a stereo microscope or magnifying glasses, neither of which is shown. Physician 15 may use other surgical tools in addition to probe 12, which are also not shown in order to maintain clarity and simplicity of presentation.

Vacuum Level and IOP During Vacuum Surge

When occlusion occurs in the aspiration channel, the IOP increases due to the continued flow of irrigation fluid into the eye. Vacuum builds in the aspiration channel/aspiration line when there is an occlusion and drops when the occlusion breaks. The drop in vacuum due to the occlusion break may cause a severe drop in IOP. Reference is now made to Graphs 110 and 111 of FIG. 1. Physician 15 typically works at a nominal IOP level 106 (e.g., 60 mmHg). As shown by curve 112 of graph 110, vacuum increases in strength (vacuum level rises) due to occlusion that occurs during phacoemulsification. At the same, as shown in graph 111, IOP increases (113).

As noted above, however, the onset of the vacuum surge, as well as the onset of a rise in IOP, are difficult to timely detect due to inherently noisy pressure and/or vacuum level reading from sensors (illustrated by actual curves 114 and 115, respectively, that exhibit fluctuations).

Automatic Real-Time Control of AVS

As noted above, in some examples, the disclosed technique uses a microcontroller comprised in a phacoemulsification probe, such as probe 12.

Figure 2:
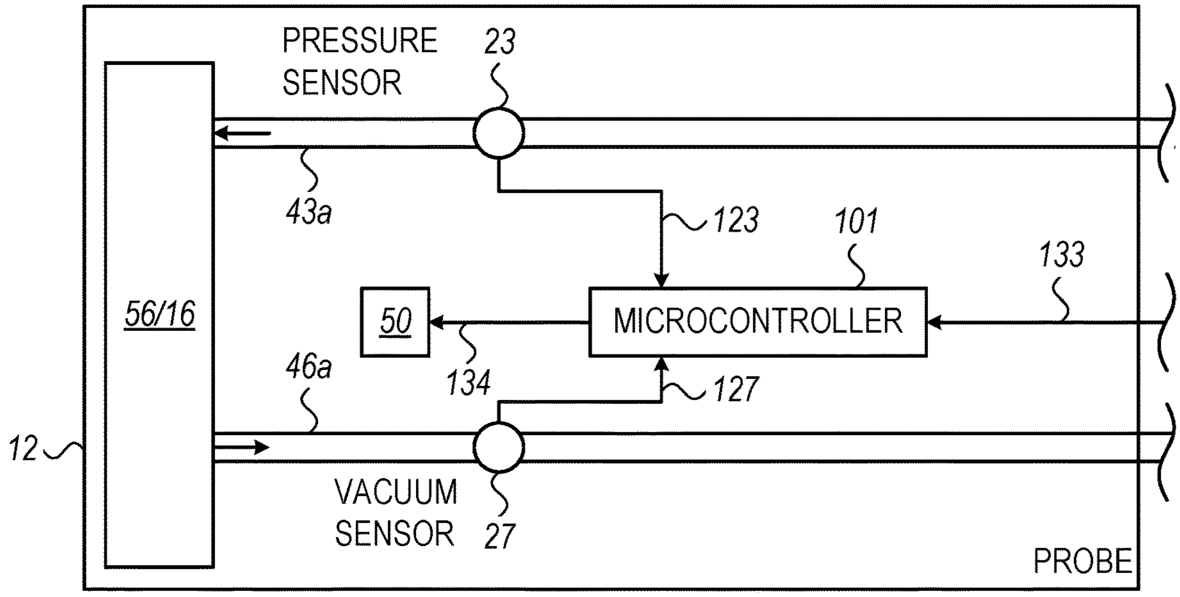
FIG. 2 is a block diagram, schematically describing a microcontroller-controlled vacuum surge suppression mechanism of the phacoemulsification apparatus of FIG. 1, in accordance with an example of the present disclosure.

FIG. 2 is a block diagram, schematically describing a microcontroller-controlled vacuum surge suppression mechanism of the phacoemulsification apparatus 10 of FIG. 1, in accordance with an example of the present disclosure.

As seen, microcontroller 101 of probe 12 receives readings from sensors 23 and 27 (e.g., pressure, vacuum, or flow) coupled respectively with irrigation channel 43*a* and aspiration channel 46*a*. These readings, received via wiring 123 and 127, are provided (e.g., sampled) in real time at a sufficiently high rate (e.g., 1 kHz) to allow a fast response time (e.g., within several milliseconds). In the shown example, sensors 23 and 27 are seen as located in handpiece 12. In general, the sensors can be located in a case or module coupled with the handpiece, e.g., by including the sensors in a disposable case coupled with the aspiration and irrigation lines just proximally of the handle itself.

A processor of microcontroller 101 analyzes the readings from sensors 23 and 27, including calculating moving averages and current CC. If a processor detects a vacuum rise that is correlated with a rise in IOP, the processor activates AVS module 50 via a wiring 134 to suppress a vacuum surge.

The example block diagram shown in FIG. 2 is highly simplified and was chosen purely for the sake of conceptual clarity. A typical microcontroller may include, for example, a more complex wiring scheme.

Figure 3:
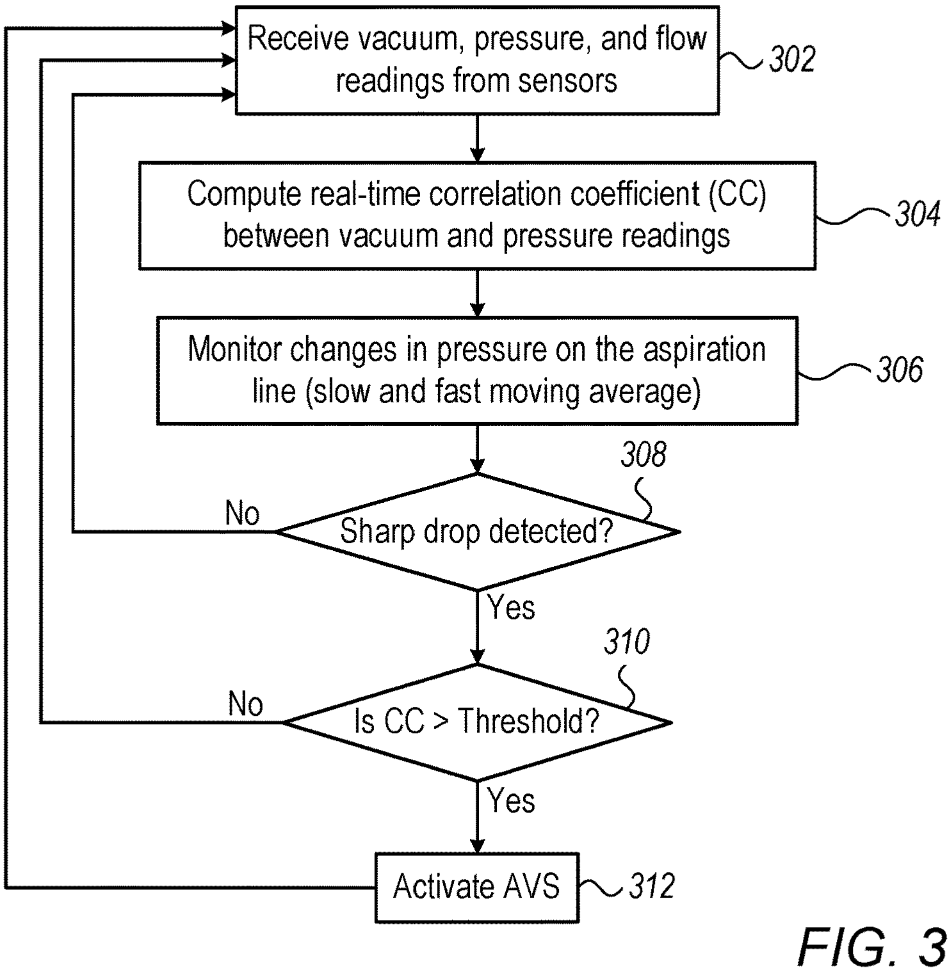
FIG. 3 is a flow chart schematically illustrating a method for automatic real-time vacuum surge suppression by the apparatus of FIG. 1, in accordance with an example of the present disclosure.

Method of Vacuum Surge Detection and Suppression Using Correlated Vacuum and Pressure Readings FIG. 3 is a flow chart schematically illustrating a method for automatic real-time control of activation of an AVS module of apparatus 10 of FIG. 1, in accordance with an example of the present disclosure.

The process assumes that physician 15 inserts phacoemulsification needle 16 of probe 12 into a lens capsule 18 of an eye 20, presses a foot pedal (not shown) to a first position to activate irrigation, subsequently to a second position to activate aspiration, and finally to a third position to vibrate needle 16 to perform phacoemulsification.

In the shown process, at aspiration vacuum level sensing and irrigation pressure and flow sensing receiving step 302, microcontroller 101 receives repeated aspiration and irrigation readings from sensors 27 and 23 (e.g., at a 1 KHz rate) during phacoemulsification.

At a correlation coefficient calculation step 304, the processor calculates real-time CC between the vacuum readings and estimated IOP.

At monitoring of vacuum surge onset 306, the processor periodically looks for a change (e.g., a fall) in sub-pressure in the aspiration line (i.e., a rise in vacuum level). To this end, the processor calculates fast- and slow-moving averages of the vacuum level. The processor compares the fast-moving average to the slow-moving average and based on the comparison can identify sharp changes in IOP. The fast-moving average provides the current base line (the larger window) and the fast-moving average provides the current pressure (small window).

When the processor detects (308) a sub-pressure drop (i.e., a stronger or risen vacuum level), the processor checks at correlation checking step 310 if the currently calculated CC value is above threshold, meaning that there is also a rise in IOP.

If the answer is yes, the microcontroller activates the AVS mechanism, as described above, at AVS activation step 312.

In either case, following steps 308 and/or 310 and/or 312, the process returns to step 302 to receive new readings. The process continuous until the phacoemulsification is terminated (e.g., completed) by the physician.

The steps of FIG. 3 are brought as an example. As another example, in addition to using readings from sensors 23 and 27, microcontroller 101 can use impedance readings from piezoelectric crystal 55, e.g., to verify tip contact with eye matter. In impedance monitoring method, the processor reads the impedance at a probing frequency close to the resonance frequency of the piezoelectric crystal 55 (e.g., at the slope of the resonance curve). At the probing frequency the impedance is highly sensitive to a shift in the resonant frequency due to change in mechanical load on the vibrating needle. As the needle is in and out of the eye matter, a change in impedance typically occurs that is indicative of the needle being in or out of the eye. The indication that the needle is in the eye can be used as a gating to applying the technique described in this disclosure, while saving its use when the needle is off the eye mater.

EXAMPLES

Example 1

A method includes calculating in real-time a correlation between vacuum readings and pressure readings of respective aspiration and irrigation channels (43*a*, 46*a*) of a phacoemulsification handpiece (12) engaged in a phacoemulsification procedure in an eye (20). Upon detecting an increase in the vacuum readings and an increase in the pressure readings, a current level of the correlation is checked. Provided that the current level of the correlation is above a given value, an anti-vacuum surge (AVS) mechanism (50) is activated, the AVS mechanism fluidly coupled with at least one of the irrigation and aspiration channels (43*a*, 46*a*) or irrigation and aspiration lines (43, 46).

Example 2

The method according to example 1, wherein estimating the increase in pressure level comprises estimating a rise in intra ocular pressure (IOP) in the eye (20).

Example 3

The method according to any of examples 1 and 2, wherein the vacuum readings are received from a vacuum sensor (27) coupled with the aspiration channel (46*a*).

Example 4

The method according to any of examples 1 and 2, wherein the pressure readings are received from a pressure sensor (23) coupled with the irrigation channel (43*a*).

Example 5

An apparatus (10) includes an interface (39) and a processor (38). The interface (39) is configured to receive vacuum readings and pressure readings of respective aspiration and irrigation channels (43*a*, 46*a*) of a phacoemulsification handpiece (12) engaged in a phacoemulsification procedure in an eye. The processor (38) is configured to (i) calculate in real-time a correlation between the vacuum readings and the pressure readings, (ii) upon detecting an increase in the vacuum readings and an increase in the pressure readings, check a current level of the correlation, and (iii) provided that the current level of the correlation is above a given value, activate an anti-vacuum surge (AVS) mechanism (50) fluidly coupled with at least one of the irrigation and aspiration channels.

Although the embodiments described herein mainly address a phacoemulsification technique, the methods and apparatuses described herein can also be used in other applications, such as with other types of electrical eye surgery tools.

It will be thus appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:

calculating in real-time a correlation between vacuum readings and pressure readings of an aspiration channel and an irrigation channel of a phacoemulsification handpiece engaged in a phacoemulsification procedure in an eye;

upon detecting an increase in the vacuum readings and an increase in the pressure readings, checking a current level of the correlation; and provided that the current level of the correlation is above a given value, activating an anti-vacuum surge (AVS) mechanism fluidly coupled with at least one of the irrigation channel and the aspiration channel.

2. The method according to claim 1, wherein the increase in pressure readings comprises estimating a rise in intra ocular pressure (IOP) in the eye.

3. The method according to claim 1, wherein the vacuum readings are received from a vacuum sensor coupled with the aspiration channel.

4. The method according to claim 1, wherein the pressure readings are received from a pressure sensor coupled with the irrigation channel.

5. An apparatus, comprising:

an interface configured to receive vacuum readings and pressure readings of respective an aspiration channel and an irrigation channel of a phacoemulsification handpiece engaged in a phacoemulsification procedure in an eye; and a processor, which is configured to:

calculate in real-time a correlation between the vacuum readings and the pressure readings;

upon detecting an increase in the vacuum readings and an increase in the pressure readings, check a current level of the correlation; and provided that the current level of the correlation is above a given value, activate an anti-vacuum surge (AVS) mechanism fluidly coupled with at least one of the irrigation channel and the aspiration channel.

6. The apparatus according to claim 5, wherein the processor is configured to estimate the increase in pressure level by estimating a rise in intra ocular pressure (IOP) in the eye.

7. The apparatus according to claim 5, wherein the interface is configured to receive the vacuum readings by receiving the readings from a vacuum sensor coupled with the aspiration channel.

8. The apparatus according to claim 5, wherein the interface is configured to receive the pressure readings by receiving the readings from a pressure sensor coupled with the irrigation channel.

* * * * *